(12) United States Patent
Sperling

(10) Patent No.: US 7,027,160 B2
(45) Date of Patent: Apr. 11, 2006

(54) DEVICE AND METHOD FOR MEASURING TRANSMISSION AND REFLECTION PROPERTIES OF OBJECTS AND SURFACES

(75) Inventor: Uwe Sperling, Geretsried (DE)

(73) Assignee: BYK-Gardner GmbH, Geretsried (DE)

( * ) Notice: Subject to any disclaimer, the term of this patent is extended or adjusted under 35 U.S.C. 154(b) by 612 days.

(21) Appl. No.: 09/834,241

(22) Filed: Apr. 12, 2001

(65) Prior Publication Data

US 2002/0005954 A1    Jan. 17, 2002

(30) Foreign Application Priority Data

Apr. 17, 2000   (DE) ................................ 100 18 982

(51) Int. Cl.
*G01N 21/47* (2006.01)
(52) U.S. Cl. ..................................................... 356/446
(58) Field of Classification Search ........ 356/445–448, 356/405–407; 250/231.14–231.17
See application file for complete search history.

(56) References Cited

U.S. PATENT DOCUMENTS

| 4,956,551 A | * | 9/1990 | Repschlager et al. .. 250/231.14 |
| 5,923,434 A | * | 7/1999 | Lex ............................. 356/445 |

* cited by examiner

Primary Examiner—Tu T. Nguyen
(74) Attorney, Agent, or Firm—Pearne & Gordon LLP

(57) ABSTRACT

The present invention relates to a device for measuring transmission and reflection properties of objects and surfaces and a method for operating said device. The device is equipped with a housing, an optical measuring base unit and preferably a source of radiation for emitting radiation at a predetermined angle onto a measurement surface, as well as a detecting means for detecting the radiation reflected from said measurement surface. An elastic retaining means serves to elastically support the optical measuring base unit in the housing such that a touchdown surface for setting down said optical measuring base unit on the measurement surface is disposed external the housing and assumes a predetermined stressed position relative the housing in the unpositioned state.

37 Claims, 9 Drawing Sheets

DEVICE AND METHOD FOR MEASURING TRANSMISSION AND REFLECTION PROPERTIES OF OBJECTS AND SURFACES

FIELD OF THE INVENTION

The present invention relates to a device for measuring visual properties, in particular transmission and reflection properties of objects and surfaces as well as a method of operating said device. The invention relates in particular to a device and a method for measuring visual properties of surfaces.

BACKGROUND OF THE INVENTION

Although the following description relates to the measurement of visual properties of surfaces, the present invention is suitable for all types of radiation, thus in particular for all kinds of electromagnetic radiation as well as for all measurements of reflection and transmission.

A device for measuring visual properties of surfaces generally has a housing in which an optical unit, respectively a base body (hereinafter referred to as optical measuring base unit) is arranged.

The optical measuring base unit comprises an illuminating means, the light of which is directed at a predetermined angle to the surface to be measured (hereinafter referred to as measurement surface). Further, the optical unit has a detecting means which receives and registers the light reflected from the measurement surface.

Illuminating and detecting means are generally arranged in corresponding receiving means of the optical unit, respectively base body.

When carrying out a measurement, the housing is placed upon a measurement surface and the measurement angles are defined by the alignment of the housing with respect to the surface. Furthermore, the housing construction generally also comprises control and evaluation electronics which receive measurement data and, for example, display same on a display means disposed on the exterior of the housing.

The illuminated area of the measurement surface is that of a predetermined section within the touchdown surface, whereby the touchdown surface and the measurement surface are brought into substantially flush planar contact with one another.

Such devices are used to characterize surfaces including, for example, products with glossy and high-gloss surfaces, goniochromatic surfaces and other such similar surfaces. A surface is goniochromatic if its characteristic optical measurement parameters, for example its color values or its reflection properties, are dependent upon the angle of illumination and measurement during a radiation measurement of said surface.

An important application in this regard is, for example, the analysis of automobile finishes. The finished surfaces are characterized during manufacture or repair in order to evaluate their quality relative to given standards.

Various devices for measuring optical properties, in particular visual properties of surfaces are known from the prior art, as are the corresponding methods thereto. Several of these measuring methods include, for example, measuring luminosity (measurement of intensity), measuring color and polarization, and other associated combined measurements.

Common to known devices and methods is that the measuring means and the measurement surface have to be in precise alignment with one another in order to provide reliable and reproducible measurement results. In other words, the angle of illumination from the illuminating means and the angle of the detecting means relative the measurement surface always have to be the same.

According to the prior art, the alignment of the measuring means to the measurement surface is registered by contact pins which are elastically affixed external the housing.

A typical arrangement is that of three contact pins defining a plane. When the optical measuring base unit is set down parallel to the measurement surface, the three contact pins are pressed inwardly and the corresponding electric contacts are closed. In contrast, when one or more contact pins are not pressed inward or are only pressed inward to an insufficient degree, the measurement is deactivated.

Despite monitoring, faulty measurements can occur.

The task of the present invention is to provide an improved device for measuring reflection and/or transmission properties of objects and surfaces and in particular visual properties of surfaces as well as a method for operating said device.

SUMMARY OF THE INVENTION

This task is solved in accordance with the present invention by the object of claim 1.

The method according to the present invention is the object of claim 35.

Preferred embodiments of the invention comprise the subject matter of the subclaims.

The invention is further characterized in that at least one detecting means, which detects at least one change in position of said optical measuring base unit relative said housing, comprises a means for determining contingencies taken from among a group of means configured for such determinations such as capacitive measuring means for deriving changes in the capacitance of a capacitor means, inductive measuring means for deriving changes in inductance, resistive measuring means for deriving changes in resistance, force measuring means for deriving changes in the force exerted on said retaining means, and other such similar means. The invention is further characterized in that said detecting means comprises at least one light barrier means, whereby at least one light barrier means emits a signal when at least a part of said optical measuring base unit undergoes a predetermined change in position. The invention is further characterized in that said housing has an interior transverse carrier means which at least comprises one partially hollow lug with a spring element supported therein, whereby at least one spring element presses against a part of said optical measuring base unit. The invention is further characterized in that said transverse carrier means is disposed with an opening through which the lugs provided on the optical measuring base unit extend into the interior of the housing, and at least one of said one least light barrier means is activated by a disk means affixed to an end of said lug.

The elastic retaining means enables the providing of a tolerance range for incorrect alignments and thus allows for reducing the amount of touchdown pressure required.

The device according to the present invention therefore ensures a general reliable monitoring of the alignment of the optical measuring base unit relative the measurement surface.

The present inventive device comprises a housing or a frame means having at least one optical measuring base unit with at least one measuring means for detecting the reflection and transmission radiation by way of at least one sensor means. This sensor means can be realized as a conventional photosensor or as a sensor means having photosensitive surfaces in rows and columns such as is the case with, for example, CCD sensors.

A retaining means is further provided for the elastic retention of the optical measuring base unit in the housing. The optical measuring base unit comprises at least one touchdown means with which the measuring base unit is positioned on the surface to be measured.

A base surface of said optical measuring base unit assumes a predetermined, yet elastically adjustable, position relative the housing in an unpositioned state. This base surface can be, for example, characterized as the underside of the measuring base unit which adjoins and is, for example, aligned essentially parallel to the measurement surface during a measurement. Likewise, every other surface of the measuring base unit may also be characterized as the base surface. Preferably, the portion comprising this surface is connected solidly to the measuring base unit and cannot move relative said measuring base unit.

The device according to the present invention has numerous advantages.

Because the measuring base unit is elastically retained in the housing according to the present invention, many flawed measurements resulting from unsuitable positioning of a measuring means upon a surface to be measured can be eliminated.

According to a preferred embodiment of the present invention, the inventive device ascertains at least one characteristic, and preferably visual characteristic, parameter of a measurement surface. Included among the relevant characteristic parameters which can be measured by the inventive device are, for example, gloss, haze, fluorescence, distinction of image (DOI), measurement surface color, etc. Furthermore, a representative measure can be determined for the typical wavelength and amplitude of the surface topology of a measurement surface at a predetermined wavelength interval, whereby to determine one or more representative measures, an evaluation may also ensue at two or more ranges of wavelength.

It is moreover possible that not only one, but also two, three or more characteristic parameters of the measurement surface can be measured, whereby it is also possible that one or more characteristics be determined for every parameter of interest.

Determining one or several characteristic visual parameters with a device according to the present invention is highly advantageous since in many optical measurements, the angle of incidence and the angle of reflection when measuring surfaces and objects have critical significance on the measurement results. Particularly with shallow angles of irradiation on surfaces, the amount of reflected radiation depends heavily on the angle of incidence so that even the slightest angular change can have a large effect on the measurement results.

The use of a device according to the present invention in which an angular inaccuracy of the optical measuring base unit during measuring is reduced is exceedingly advantageous since this increases measurement accuracy and reproducibility.

Preferably, the base surface of the optical measuring base unit has a contact surface, which during measurement, respectively in the positioned touchdown state, is at least partially in contact with the surface to be measured.

In a preferred embodiment of the present invention, the touchdown means, with which the device is placed upon the surface to be measured, has at least one base, contact or supporting means. Depending on the design of the supporting means, it is to be preferred that two, three or more supporting means are provided, of which essentially each one has contact at least partially with the surface to be measured during measurement. The base surface can in this case also be defined as a contact surface of one or more supporting means with the surface to be measured.

Preferably, the supporting means has a length-adjusting means which enables the length of each respective supporting means to be elastically adjusted.

The present embodiment is particularly preferred since at least two different elastic means are provided, namely one as the retaining means for an elastic retention of the measuring base unit and the other as one, respectively several, supporting means, the length of which can likewise be adjusted elastically. Such a configuration is highly advantageous since a particularly resilient distribution of the pressure force exerted by the user is granted to the surface to be measured so that a compensation and a distribution of the pressure force, respectively the force of pressure among the various elastic means ensues so that an exact alignment during measurement is achieved and, thus, measurement precision is increased.

Preferably, the retaining means comprises one guiding means; two guiding means is particularly preferred. Said guiding means are preferably realized such that the measuring base unit is arranged in the housing to be displaceable in at least one direction, wherein especially preferred is the measuring base unit being arranged in the housing to be displaceable perpendicular to a measurement surface. Particularly preferred is at least one guiding means comprising a reset means so that in a condition in which the device is set down properly on the measurement surface, a resetting force will be exerted on the measuring base unit, on the housing respectively.

In a further preferred embodiment of the present invention, a detecting means is provided which registers a change in position or pressure in the touchdown means. This is highly advantageous since it allows the determining of the position of and/or the pressure force on the measuring base unit and same can then be taken into account during measuring and during evaluation of the measurement.

It is particularly preferred that the alignment of the base surface to the measurement surface is determinable in order to detect any deviation of the measurement plane from the target reference plane and, if necessary, to compensate for same so that such errors in alignment can be discounted from the measurement values during measurement in order to obtain correct characteristics, respectively characteristic parameters.

To this purpose, the detecting means can detect a change in position of the measuring base unit at at least one point substantially perpendicular to the measurement surface.

In preferred embodiments, the detecting means can determine and/or derive a change in position by way of, for example, a change in capacitance in a capacitive means, a change in inductance in an inductive means, a change in resistance in a resistive means, or a change in force in, for example, the retaining means.

It is hereby possible, for example, that the capacitance of a capacitor is changed due to the introduction of a dielectric medium between its capacitor plates or that an immersion pin immerses in a coil means and modifies the inductance of said coil means. Should a sensor or several such sensors be used to determine the position, respectively the change in position of the optical measuring base unit, the position of said measuring base unit, and thus the alignment of the optical components to the measurement surface, can be determined. In this way, the reliability and the accuracy of the measurement can be increased so that, on the one hand, production processes can be optimized and, on the other hand, a more precise classification of components is granted.

It is also possible that the detecting means detect a change in pressure in the contact surface between the touchdown means and the surface to be measured, wherein the detecting means can function as a capacitive and/or as a local resolution detecting means.

In another preferred embodiment, at least one light barrier means is provided for emitting a signal when the optical measuring base unit undergoes a predetermined change of position such as, for example, exceeding or falling short of an admissible range for deviations in the alignment of base surface to measurement surface. Such an embodiment is highly advantageous since measurement errors can substantially be reliably prevented because the user is made aware of such measurement conditions.

According to a further embodiment, one pressure means of at least one of said at least one retaining means can urge the optical measuring base unit toward an inner surface of the housing, respectively housing frame. This pressure means can be realized, for example, as a spring means such as, for example, a helical spring, or as a rubber and in particular a hard rubber means, or any other such similar means, wherein leaf spring and cup spring pressure means are also possible.

In accordance with a preferred embodiment of the present invention, the housing comprises an internal carrier means.

A further preferred embodiment provides for an activation means to activate a measurement when a suitable alignment of the base surface to the measurement surface is evident, wherein in particular it is also possible that the activating means releases a blocking of the measuring process so that a user can only trigger a measurement by actuating of a triggering means when the alignment of the base surface to the measurement surface is within a permissible and predetermined range.

Such a configuration of the invention is of great advantage since a measurement can only then be triggered upon a suitable alignment of the base surface, and therefore the suitable alignment of the optical measuring means, to the surface to be measured. One of the most crucial reasons behind many faulty and erroneous measurements is thus fundamentally eliminated.

In a further preferred embodiment of the invention, at least one retaining means urges the optical measuring base unit in the direction of an inner surface of the housing by means of a pressure means. Said pressure means can be any means which generates pressure. Preferred are spring means, rubber means or means made from elastic, resilient material such as, for example, foam or durofoam. In particular, helical springs or hard rubber means are preferred. Such a pressure means generates a tensioning of the measuring base unit to the housing.

In a preferred embodiment of the present invention, a carrier means is disposed within the housing. One or more partially hollow lugs may be provided thereupon, each of which can respectively comprise at least one spring element arranged therein, wherein said at least one spring element is braced on one side against said carrier means and on the other side against the measuring base unit so as to attain an elastic supporting of the measuring base unit in the housing. The part at which the spring elements are braced to the measuring base unit can be configured in plate-shaped form and in particular can also be a circuit board means.

In the latter described embodiment, it is also possible to arrange an elastic medium between the carrier means and the measuring means which can essentially also be made of foam or durofoam. Furthermore, it is possible to arrange such a durofoam means in a flat region between the carrier means and the measuring base unit while the carrier means is additionally provided with lugs having the corresponding spring elements.

Such an embodiment is highly advantageous since it allows the achieving of a resilient and elastic positioning of the measuring base unit. In a preferred embodiment of the invention, wheels can be arranged on the housing and/or on the measuring base unit, so that the inventive device can be moved over the surface to be measured during a measurement in order to facilitate a plane measurement.

In a further preferred embodiment of one or more of the previously described embodiments, the measuring base unit is further provided with at least one source of radiation, the emitted radiation of which is at least partially directed at a predetermined angle onto the surface to be measured. Preferably, the source of radiation emits electromagnetic radiation and light in particular.

Having the device according to the present invention comprise a source of radiation is highly advantageous since this enables carrying out measurements of the visual properties of a surface without the need for an external source of light or radiation. Simply by positioning the device on a surface to be measured, the measurement is triggered. In contrast hereto, a device without a source of radiation would require an external source of radiation in order to perform a measurement. On the other hand, in the case of there not being an integrated source of radiation, it becomes advantageous that a source of power, such as for example a battery or storage cell, will be needed only to supply energy to the sensor and the evaluation electronics.

In a preferred embodiment of one or several of the previously described embodiments, the housing is capable of being set upon the surface to be measured in such a manner during a measurement that at least one part of said housing is in preferably direct contact with the surface to be measured. It then becomes possible that, for example, the housing is set down upon the surface together with a frame or similar means such that in the case of, for example, an even surface, a lower edge of the device will be wholly positioned upon the surface to be measured. However, it is also possible that the underside of the housing be of a curved form (concave, convex, etc.) so that in the same case of an even surface, only two edges of said device position onto the surface to be measured.

Such a configuration is extremely advantageous since the housing is positioned firmly upon the surface to be measured during measurement and the aligning of the optical measuring base unit to the surface to be measured as rendered by the elastic retaining means may then transpire essentially automatically.

In the present preferred embodiment, it is furthermore preferred that the optical measuring base unit is essentially surrounded on all sides (except for the measuring side) by the housing. When performing a measurement, the user holds the device by its housing and thus basically cannot come into any contact with the optical measuring base unit at all. This is particularly preferred when the optical measuring base unit is capable of aligning automatically to the measurement surface in at least one direction. Any potential falsifications to a measurement resulting from a user coming into direct contact with the measuring unit can thus be avoided.

In another embodiment in which no part of the housing comes into contact with the surface to be measured during a measurement, the user holds the device by its housing and places said device with the touchdown means of the optical measuring base unit on the surface to be measured thereupon. The user presses the device down onto the surface such that the optical measuring base unit exhibits a suitable alignment to the surface to be measured. Such a configuration is highly advantageous since, as a result of positioning of the device on the surface and based on the direction and magnitude of the user's applied pressure, diverse opportunities are granted for influencing the alignment of the device during measuring and, thus, the measurement results. This is quite advantageous in comparison with a rigid measuring device in which improperly setting down of the device, surface unevenness, dust particles, etc., can lead to a falsification of measurement results, a contingency which a user is to avoid.

On the other hand, a configuration according to the latter described embodiment, in which at least one part of the housing of the device remains in contact with the surface to be measured, is highly advantageous since the user positions the device on the surface to be measured by way of the housing, thereby exerting pressure such that the housing contacts the surface to be measured. The elastically retained optical measuring base unit is then likewise in contact with the surface to be measured and can, since it is of an elastic retention, align itself automatically to the surface to be measured. A plurality of measurements thus ensue which are of fundamentally identical positioning and measuring conditions.

In a further preferred embodiment of the present invention, the housing encompasses at least one housing supporting means; two housing supporting means are preferred and at least three housing supporting means are especially preferred. In positioned touchdown state, the housing supporting means is at least partially in direct contact with the surface to be measured. Should only two housing supporting means be provided, same are preferably of elongated configuration so that a secure footing is established upon touchdown of the housing on the surface to be measured. Should three or more housing supporting means be provided, they may be of slimmer configuration and may have, for example, a conical or a tapered shape whereby it is preferred that the ends which are directed to the surface to be measured are rounded and have a large radius so as to fundamentally exclude any instance of the surface to be measured being scratched upon setting the housing down atop said surface to be measured.

An especially high measurement reproducibility is attained particularly when utilizing three housing supporting means which are of, for example, cylindrical configuration, since three touchdown points allow for an exact defining of the position of the housing on the surface to be measured.

In another preferred embodiment of the present invention, at least one part of the optical measuring base unit protrudes from said housing in the non-positioned state, whereby especially preferred is that at least one part of the touchdown means extends out from said housing.

In a further preferred embodiment of the present invention in which the housing is in at least partial contact with the surface to be measured during measurement, it is then preferable that touching the housing down upon the surface to be measured induces a displacement of the optical measuring base unit within the housing.

In another preferred embodiment of the present invention, the optical measuring base unit is universal-mounted in the housing or pivotally arranged through at least one range of angles relative to at least one pivotal axis and especially preferred is that said pivotal axis is aligned essentially parallel to the surface to be measured.

In a further preferred embodiment, the optical measuring base unit can rotate about two axes, both of which are aligned essentially parallel to the surface to be measured. Said two pivotal axes are preferably essentially perpendicular to one another.

It is highly advantageous for the optical measuring base unit to be rotatable about one axis in the housing, since same can then be aligned in at least one direction to the surface to be measured. This translates into a considerable facilitation for the user, since all that he must pay attention to during touchdown positioning is that the device is not, for example, tilted longitudinally.

When, on the other hand, the optical measuring base unit is arranged to be rotatable around two axes, the user must simply set the device down upon the surface to be measured. The larger number of movable parts, however, does raise the probability of failure. The mechanical expenditure and thus the cost of the device likewise increase correspondingly.

In another preferred embodiment of the present invention, at least one pivotal axis is aligned essentially perpendicular to a connecting segment between two of said supporting means of said optical measuring base unit. Especially preferred is that the pivotal axis is arranged essentially central between said two supporting means so that the optical measuring base unit can also be regarded as a kind of a seesaw with one of said one supporting means at one end and the other of said supporting means at the other end.

Especially preferred in the present embodiment is that the pivotal axis is arranged close to the surface to be measured. One of the main advantages of this arrangement is that transverse force is kept small. It is especially preferred that the distance of the pivotal axis from the surface to be measured is smaller than a length of the connecting segment between the supporting means; particularly preferred is that said distance is smaller than half or a third of the length of the connecting segment between said supporting means. Such a configuration allows an especially large torque to be exerted on the seesaw (the optical measuring base unit) when one supporting means is extended farther than the other.

In a further preferred embodiment of the present invention, at least one of said at least one pivotal axis is positioned in the supporting means of said housing; especially preferred is the rotatable positioning of the pivotal axis on the guiding means of said supporting means.

It is preferred that the entire optical measuring base unit is connected with the guiding means and thus the supporting means of the housing via the pivotal axis so that, on the one hand, the optical measuring base unit can be pivoted about the pivotal axis and, on the other hand, be arranged flexibly displaceable in the guides of the retaining means.

Such an arrangement is highly advantageous, particularly in the configuration in which a part of the optical measuring base unit protrudes from the housing in the non-positioned state, since upon touching the device down on a surface to be measured, the optical measuring base unit is then urged along the guiding means into the housing while still remaining pivotal about at least one pivotal axis in the housing. Upon the housing then being positioned firmly on the surface to be measured, the alignment of said optical measuring base unit then follows essentially automatically through the equilibrium of forces of the elastic components involved such as, for example, the elastically retained supporting means of the optical measuring base unit and the elastic retaining means in the housing.

In a further preferred embodiment of the present invention, at least one clearance distance from the surface to be measured can be defined for at least two points on the housing and/or the base measuring unit. Preferably, said at least two points are arranged on facing points of said housing and/or base measuring unit.

Measurement of the clearance to the surface to be measured preferably transpires by means of a transmitting means emitting a signal, whereby the signal reflected from the surface is received by a receiving means and then evaluated in tandem by evaluation electronics, resulting in at least one clearance characteristic being derived for the distance from the surface to be measured.

The transmitting means preferably makes use of electromagnetic and/or sound waves and evaluating the clearance transpires utilizing a procedure such as, for example, running time measurement, triangulation, or interference evaluation.

Clearances at clearance measurement points are known for an ideal even surface so that a representative measure of any curvature of a measurement surface can be determined from the clearance characteristics as measured. Should the distances be greater than those for an even surface, this indicates a surface curved outwardly; smaller distances indicate a surface curved inwardly.

The determining of a value of curvature for the surface to be measured is quite advantageous since curved surfaces have the potential to influence especially visual measurement results in that, for example, a focusing or defocusing of the optical radiation can result which can conceivably have a considerable effect on the signal intensity of the light received by the photosensor. Should a representative measure of surface curvature be determined, same can be taken into account with respect to the measurement results and any curvature can thus be discounted.

In another preferred embodiment of the present invention, a pattern projection means is provided for projecting a light pattern onto the surface to be measured in which a sensor means receives the light reflected by the measurement surface. Providing a photosensor comprising light-sensitive elements arranged in rows and columns, for example a CCD array sensor, is especially preferred as said sensor in this embodiment. In this preferred embodiment, a curvature characteristic for the measurement surface is calculated by evaluating the light intensity profile of said photosensor and by a determining of the progression of light lines or light/dark edges in the pattern as mapped. Said light pattern herewith preferably encompasses light/dark edges and, for example, parallel lines, concentric circles or a cross-grid pattern, etc.

It is preferable in the present embodiment that at least one second sensor means is provided in the optical measuring base unit for the purpose of receiving said light pattern image. Should only one sensor means be provided, the light pattern can be projected, for example, periodically or at the push of a button and measurement values can likewise be taken, for example, periodically.

In a further preferred embodiment of the present invention, should a tilting of the optical measuring base unit relative the surface to be measured be determined during the course of taking measurement values, the received measurement values can be corrected and the characteristic parameters to be determined defined with the corrected measurement values.

Such an embodiment is highly advantageous even when, for example, the base measuring unit aligns fundamentally automatically to the surface to be measured, since the determining of a tilting allows for taking even the slightest angular inaccuracies into account when deriving parameters or when assessing said parameters.

In another preferred embodiment of the present invention, a length control means is provided in one or preferably in essentially each supporting means of the optical measuring base unit, so that at least one length of at least one supporting means may be adjusted.

It is further preferred that at least four clearance sensors are arranged in such a manner on the optical measuring base unit that at least one tilting of said optical measuring base unit relative the measurement surface can be determined. For example, a Wheat stone bridging circuit means can furthermore be provided; the output signal of which can be used to control the length control means of the supporting means so as to attain an alignment of the base surface to the measurement surface which is within a permissible range.

Such an embodiment is of particularly great advantage since it allows actively obtaining a befitting alignment of the optical path of radiation to the measurement surface.

The inventive device and inventive method can be employed, for example, in order to modify the measurement results attained with the following known devices and methods:

A device for measuring the reflection properties of surfaces is known from DE 44 34 203 A1, having a first optical means comprising a light source for directing the light emitted by said light source at a predefined angle to the measurement surface.

A second optical means is provided, likewise aligned at a predefined angle to said first optical means and to said measurement surface, and which receives the light reflected from said surface. Said second optical means of this known device comprises at least three photosensors which are arranged so as to measure the intensity of the reflected light in ranges which correspond to various different angles of reflection.

A control means is furthermore provided for controlling the device and registering the signals emitted by said at least three photosensors. The light-sensitive surfaces of these photosensors are hereby arranged essentially on one plane. Said photosensors form an integrated component, whereby a common substrate is provided on which light-sensitive layers are arranged and which detect amounts of incident light essentially independently from one another. The light-sensitive layers are arranged such the light-sensitive surfaces each detect an amount of light reflected within a predefined range of angles.

A method and a device for a quantifiable assessment of the physiological impression of reflecting surfaces is known from DE 41 27 215 A1 having a point light source, the light emitted therefrom reflected by a surface to be measured and detected by a photodetector.

A plurality of surface measurement values are derived from these brightness values for a number of various measurement points at a defined distance from one another, in which a number of preceding and succeeding brightness values are respectively taken into consideration. This enables determining and analyzing the wavelength of surface irregularities. A quality parameter for the assessing of the respective surface is derived from the ascertained surface measurement values.

The present device can be equipped with measuring wheels which rotate upon coming into contact with the surface, their rotational motion used to establish the individual measurement points.

DE 44 34 203 A1 describes a device for measuring the visual properties of surfaces in which the detector means as provided has at least three photosensors which are arranged so as to measure the intensity of the reflected light in ranges which correspond to various different angles of reflection.

BRIEF DESCRIPTION OF THE DRAWINGS

Further advantages, features and application possibilities of the present invention will now be yielded in the following detailed description of embodiments in association with the drawings, which show.

DETAILED DESCRIPTION OF THE INVENTION

Figure 1:
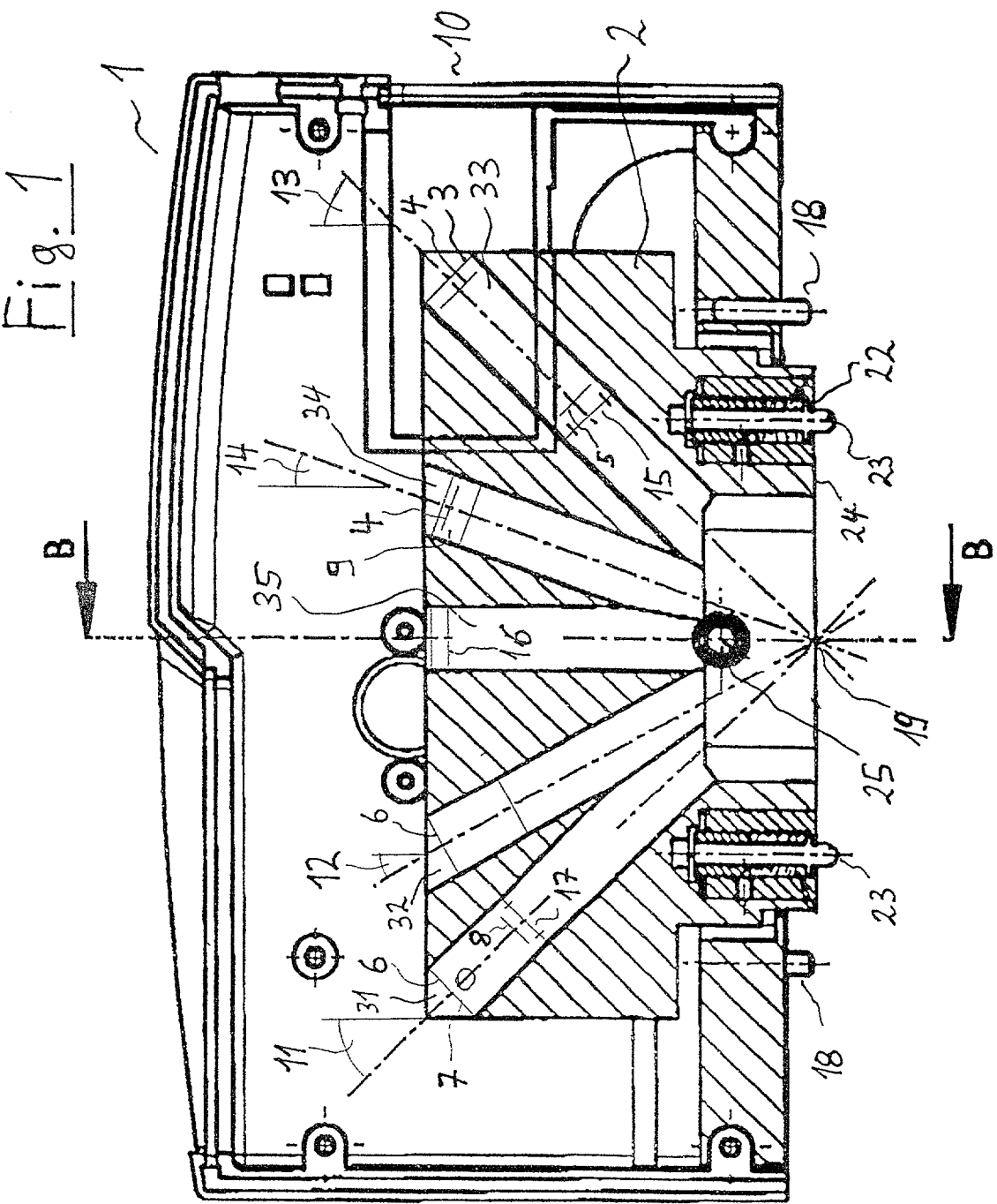
FIG. 1 a longitudinal side view of a first embodiment of the device according to the present invention.

The same reference numerals in the various figures always refer to the same components.

Figure 2:
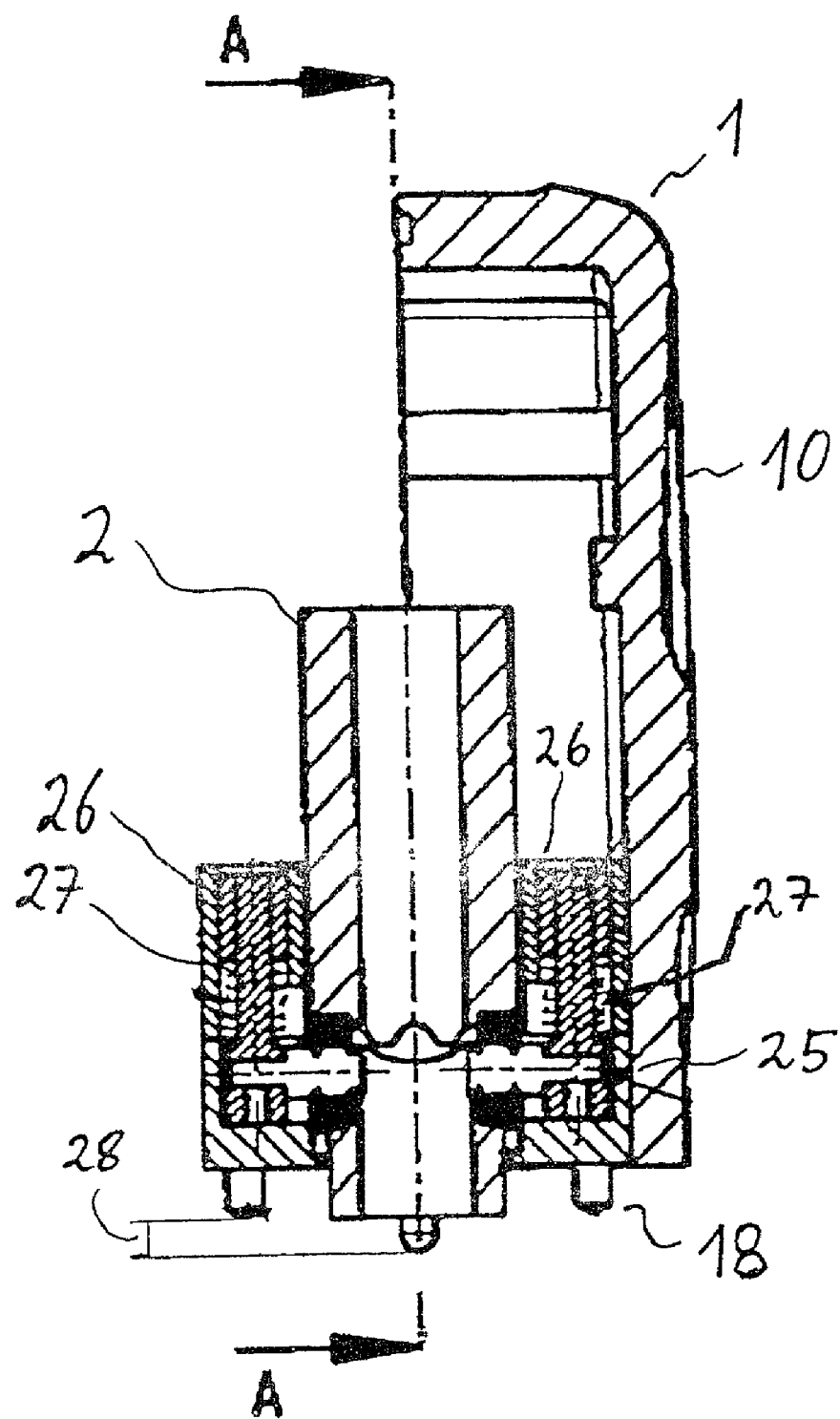
FIG. 2 a cross-sectional side view of the embodiment according to FIG. 1.

FIGS. 1 and 2 depict a first embodiment of the inventive device 1, here configured as a hand-held measuring device.

FIG. 1 shows a longitudinal section along A—A from FIG. 2 and FIG. 2 shows a section along B—B according to FIG. 1.

Measuring device 1 comprises an optical measuring base unit, optical unit 2 respectively, in which a number of drill holes 31, 32, 33, 34, 35 are disposed. Each of said holes 31–35 is directed at a precisely defined angle 11, 12, 13, 14 to the vertical of a measurement surface.

An optical illuminating means 6 is arranged in each respective hole 31, 32, whereby each of said illuminating means 6 comprises a light source 7, configurable as, for example, a laser, a light-emitting diode or a thermal emitter such as a halogen bulb. Said optical illuminating means may additionally comprise a lens 8 and an aperture means 17 in order to, for example, parallelize the light emitted from light source 7 or to radiate defined convergent or divergent light. For this reason, the distance of lens 8 from light source 7 may also be adjusted.

The light emitted by illuminating means 6 strikes measurement surface 19 at predefined angle 11, respectively 12, where it is reflected according to the laws governing reflection.

The light emitted at angle 11 and then reflected is received by a measuring means 3, arranged at angle 13, and detected by a photosensor 4. Measuring means 3 may comprise a lens 5 as well as an aperture 15 in order to, for example, parallelize the received light or to focus it onto the sensor. To this end, the distance between lens 5 and photosensor 4 may be adjusted in order to adapt the measuring device to different measuring conditions and needs.

A second measuring means 9 is arranged in a further receiving hole 34 disposed at an angle 14. Said measuring means 9 may be configured identical to measuring means 3.

In the present embodiment, illuminating means 6 and measuring means 3 and 9 are arranged symmetrically to one another.

Optical unit 2 is furthermore disposed with a drill hole perpendicular to the surface in which measuring means 16 is arranged which serves to, for example, measure the color of a surface. Measuring means 16 is designed such that it can detect radiation of different wavelengths and comprises three sensors of differing spectral sensitivity for detecting a color of a surface.

The other measuring means can be designated for the determining of the gloss, haze, surface ripple or orange peel, or other visual characteristic parameters.

In the present embodiment, the optical unit is disposed with two suspended bases 21 with which said optical unit 2 is set upon the surface to be measured during a measurement.

Each of said base 21 is elastically mounted in optical unit 2, whereby each helical spring 22 respectively backs a stud region of said base out of optical unit 2 in home position.

Three fixed bases made of solid material are provided on housing 10 of measuring device 1, at least two of them being so configured that they have a fixed but adjustable length. This can ensue, for example, in that a threading is provided on the base for screwing same into housing 10 of the measuring device. A headless screw (not shown) can serve, for example, for setting base 18 after calibrating the measuring device.

Optical unit 2 is rotatably braced about pivotal axis 25 in housing 10, so that optical unit 2 can be pivoted at least to some degree in housing 10.

Pivotal axis 25 for the rotatable supporting of optical unit 2 is braced by way of two guiding means 26 in housing 10 of measuring device 1. Each guide comprises a spring 27 which pre-stresses pivotal axis 25 and thus optical unit 2. Springs 27 in guides 26 urge optical unit 2 out of housing 10 of measuring device 1, so that base 21 of optical unit 2 protrudes downwardly out of housing 10 when the measuring device is in an unstressed state, respectively not positioned on a measurement surface.

In home position, said suspended bases 21 of optical unit 2 protrude from the underside of housing 10 at a clearance 28 past base 18 of housing 10.

Should measuring device 1 now be placed horizontally upon an even measurement surface, contact surfaces 23 of suspended bases 21 first come into contact with the surface to be measured. This stresses springs 22 of suspended base 21, so that base 21 moves somewhat into optical unit 2.

A force is exerted on optical unit 2 which is transferred via pivotal axis 25 onto guides 26 and stresses springs 27.

As a result, the optical unit is shifted along guides 26 into housing 10 of measuring device 1, so that upon a certain touchdown pressure being exerted, contact surfaces 23 of optical unit 2 will be introduced into housing 10 by a measure of clearance 28. Fixed bases 18 of housing 10 then come into contact with the surface to be measured.

Thus, the pressure the user needs to apply during measuring is lowered since the user only increases pressure until he perceives a solid resistance. If such solid resistance would not be perceived, it is conceivable that the user would continue to increase a heavy pressure and would quickly become unnecessarily fatigued or even damage the surface to be measured due to applying too large of a force. In addition, precisely defined and reproducible conditions are established.

Figure 3:
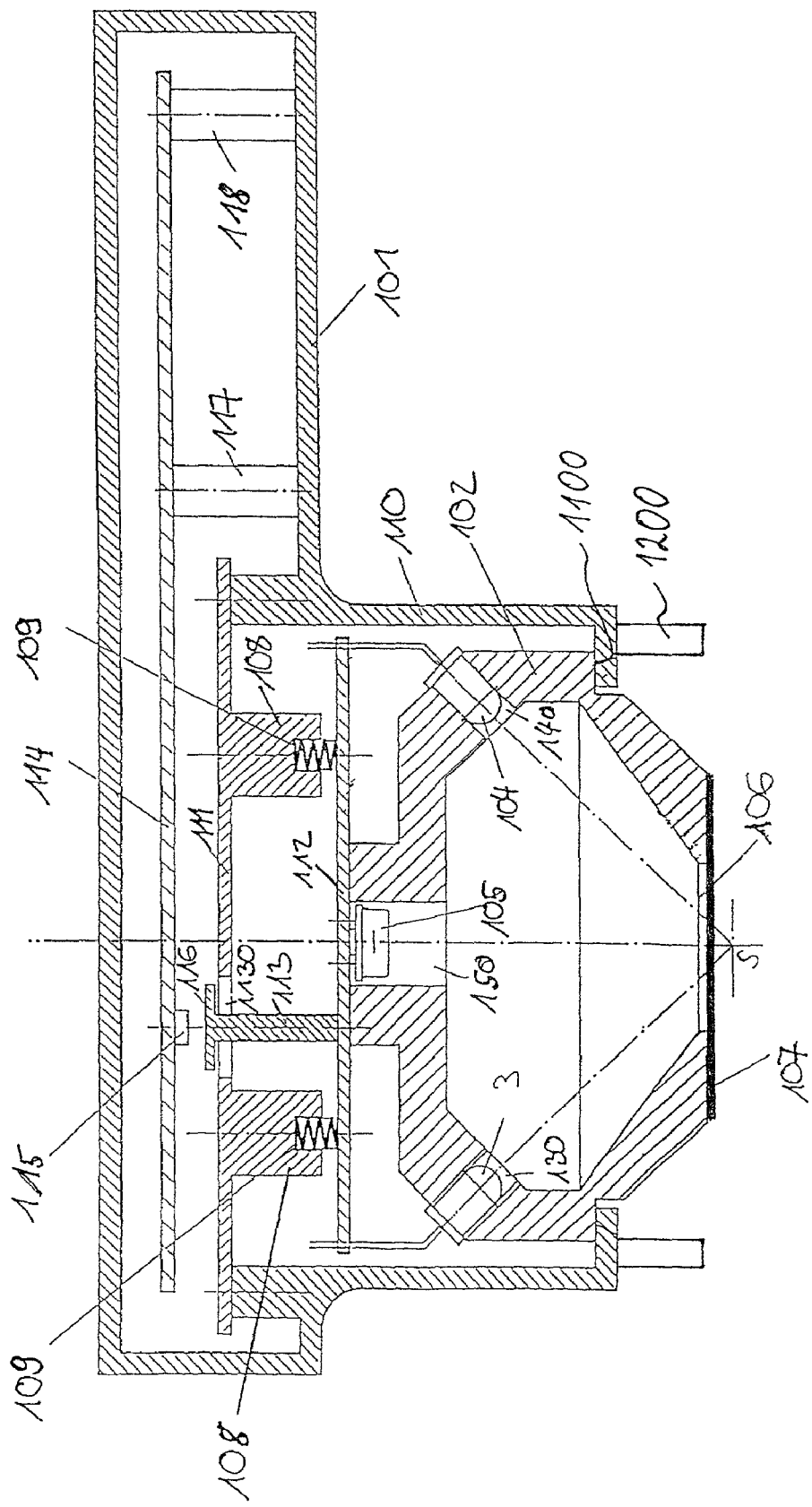
FIG. 3 a second preferred embodiment of the inventive device.
Figure 4:
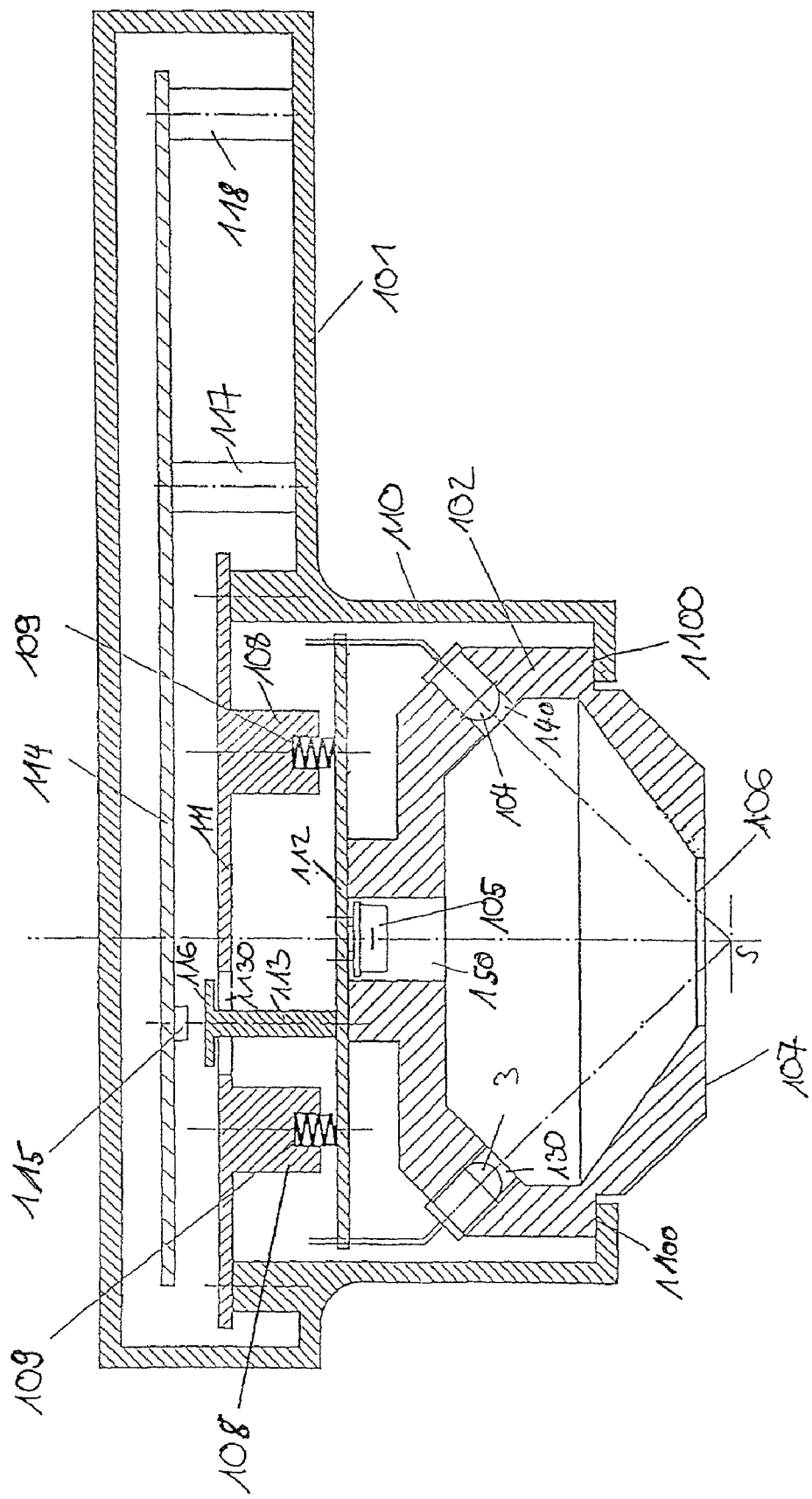
FIG. 4 a cross-sectional view of a third preferred embodiment of the device according to the present invention.

FIGS. 3 and 4 show a cross-sectional view of a second and third preferred embodiment of the device according to the present invention.

Reference numeral 101 in FIGS. 3 and 4 designates a housing in which optical measuring base unit 102 is disposed. Three illuminating means 103, 104 (one of said illuminating means is not recognizable in this cross-sectional view) and a detecting means 105 are housed at predetermined positioned angles in said optical measuring base unit 102 in the corresponding cylindrical receiving holes 1130,1140, 1150. Other configurations provide for six, twelve or more symmetrically distributed illuminating means. The beams of light emitted from said three illuminating means 103, 104 exit the optical measuring base unit 102 through an opening 106 and intersect at a point S on the measurement surface (not shown) external said optical measuring base unit 102. Detecting means 105 is positioned exactly above said point S and detects the beam of light reflected in its direction.

Said three illuminating means 103, 104 and said detecting means 105 are linked to control and evaluations electronics via not shown connections located on a circuit board 114 within housing 101, whereby said circuit board 114 is connected to said housing 101 by way of mounting means 117, 118.

Both illuminating means 103, 104 are preferably LEDs, and detecting means 105 is, for example, a photodetector.

Furthermore, reference numeral 107 designates a touchdown surface which is the lower external surface of optical measuring base unit 102 and which, as described above, must be aligned parallel to the measurement surface during the measurement procedure.

Touchdown surface 107 can itself be positioned directly upon the measurement surface or it may also be first provided with a coating of a suitable material such as, for example, Teflon, for the purpose of avoiding any damaging of the measurement surface when positioning. It is also possible to provide wheels on housing 101 and/or on optical measuring base unit 102 which keep touchdown surface 107 at a distance from the measurement surface and simultaneously enable a detecting of the relative movement of the measurement surface with respect to the device.

Figure 5:
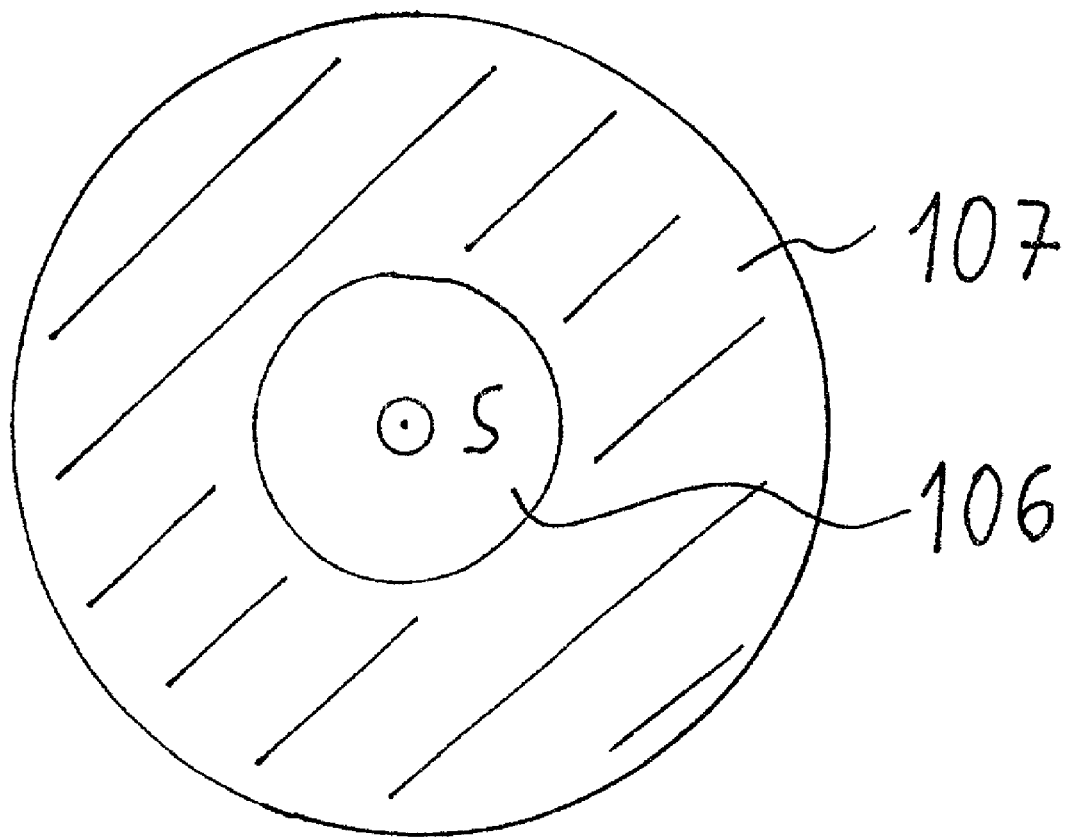
FIG. 5 an underside (enlarged) view of the touchdown surface of the optical measuring base unit of FIG. 4.

FIG. 5 shows an underside (enlarged) view of touchdown surface 107 of optical measuring base unit 102.

Again making reference to FIGS. 3 and 4, the optical measuring base unit 102 is partly enclosed by a profile 110 which is a part of housing 101. Profile 110 has an inwardly directed lip which comprises a bed region 1100 upon which the corresponding overhang of optical measuring base unit 102 rests when the device is not positioned on the measurement surface.

An elastic retaining means is further provided in the form of spring element 109, which presses optical measuring base unit 102 against bed region 1100.

Said spring element 109 is preferably housed in a partially hollow lug 108 disposed on a carrier means 111 in the interior of housing 101 and exerts a predetermined pressure against plate-shaped region 112 provided on optical measuring base unit 102. The number of spring elements 109 and corresponding partially hollow lugs 108 is contingent upon the size and the shape of the optical measuring base unit 102.

Preferably, at least three partially hollow lugs 108 and three spring elements 109 are provided which are preferably arranged in an approximate circle essentially parallel to the touchdown surface, the center of which is essentially vertically above the measurement point.

A thin F*ig*. 113 disposed on the circuit board, respectively the plate-shaped region 112, extends through opening 1130 in carrier means 111 into the interior of housing 101, where circuit board 114 is likewise housed.

A light barrier means 115 is disposed within the housing, preferably on circuit board 114; disk 116 affixed to an end of thin finger 113 can interrupt same when said thin finger 113 is moved vertically upward corresponding to the movement of optical measuring base unit 102 counter the pressure of spring element 109 when being set down upon on the measurement surface. Light barrier means 115 is linked to the control and evaluation electronics disposed on circuit board 114 and controls the measurement procedure and activates or deactivates same.

The following will explain the operation of the device:

Housing 101, which when assembled has the approximate dimensions of a thick paperback book, is held in the hand of a user and placed on the measurement surface. The touchdown pressure induces that the optical measuring base unit 102 moves from its position in unpositioned state counter the pressure of spring element 109, whereby the pressure of said spring element 109 on the plate-shaped region 112 simultaneously changes due to compression of said spring element 109.

Position and pressure change are contingent upon the manner in which the optical measuring base unit 102 is set down on the measurement surface, and therefore allow for the definition, detection and monitoring of the correct measurement position.

Should surface touchdown transpire such that a correct measurement position has been assumed; i.e., the touchdown surface and the measurement surface approximate the parallel state, the optical measuring base unit 102 is then shifted along its guides such that the light barrier means 115 is activated by disk 116 on thin finger 113. This is followed by the control and evaluation electronics activating the measurement.

It is possible in a preferred embodiment to detect when the optical measuring unit is touched down in a tilted manner. Light barrier means 115 will then not close and, accordingly, no measurement will be activated by the control and evaluation electronics, since the optical measuring base unit 102 does not move correspondingly in its guides.

It is possible in a preferred configuration that after correct initial touchdown of optical measuring base unit 102, the user exerts a certain torque which tilts optical measuring unit 102 correspondingly. At a predetermined position, light barrier means 115 will then re-open as a result of which the measurement will again be interrupted by the control and evaluation electronics.

The elastic retention of the optical measuring base unit thereby ensures that slight changes in direction and/or dimension of the touchdown pressure do not induce position changes into an incorrect position once the optical measuring base unit has assumed the correct measurement position.

In other words, the elastic retention enables compensating for changes in direction and/or dimension of the touchdown pressure. This compensating function can considerably reduce the number of faulty measurements when operating the device. Preferably, an alarm means indicates to the user any departure from a correct measurement position, meaning departure from the compensating realm.

When positioning, first the touchdown surface comes into contact with the measurement surface.

In the embodiment in accordance with FIG. 3, base 1200 of the housing touches down on the measurement surface at a defined touchdown pressure so that the user realizes from the resistance that the pressure as applied is sufficient.

In the example according to FIG. 4, the user himself must decide whether the force exerted is sufficient.

Figure 6:
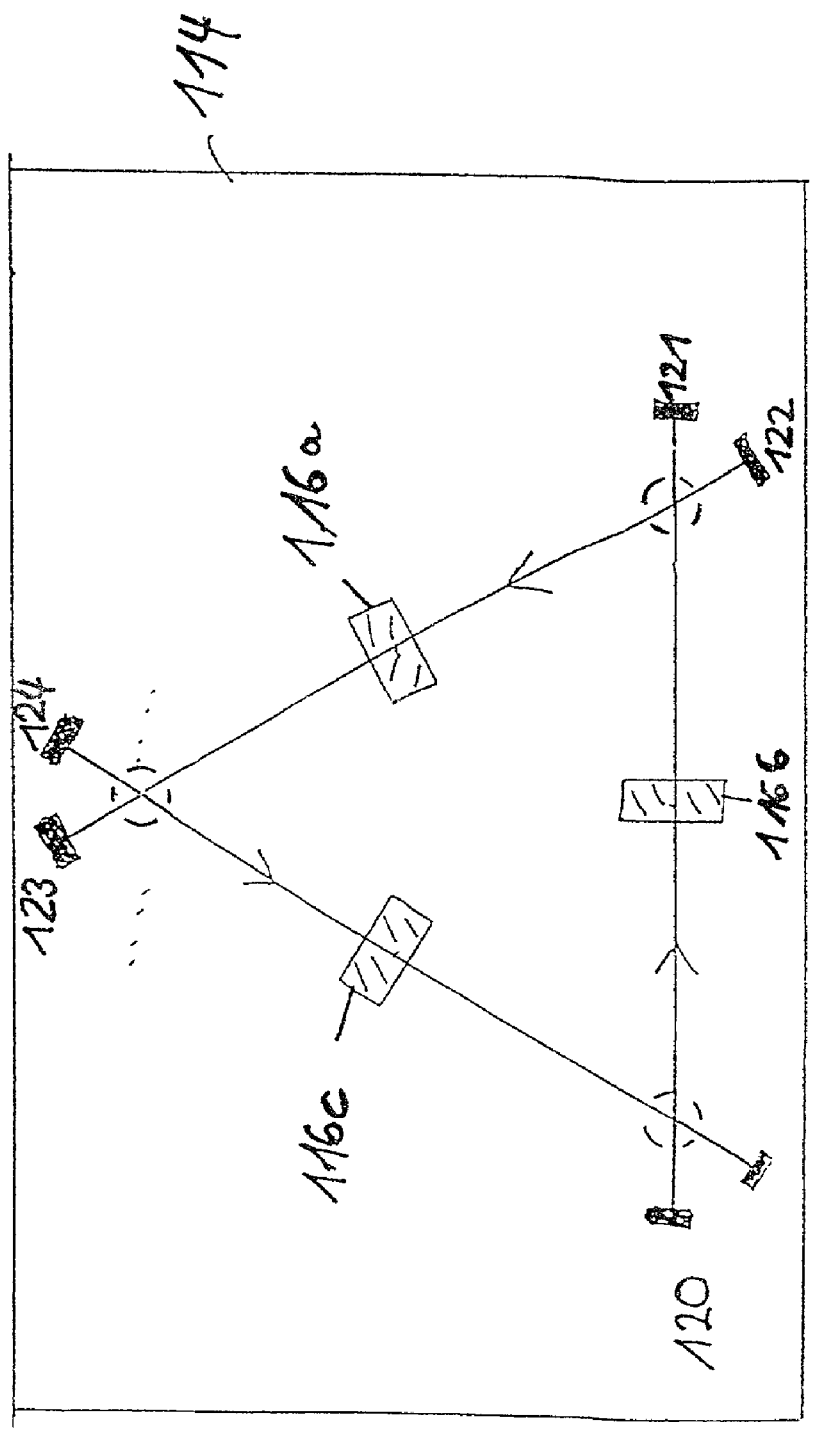
FIG. 6 a view from above of a preferred light barrier means from the third embodiment of the device according to the present invention.

FIG. 6 represents a view from above of a preferred light barrier means from the third embodiment of the device according to the present invention.

As FIG. 6 shows, a first light barrier 120, 121, a second light barrier 122, 123, and a third light barrier 124, 125 are provided in triangular-like arrangement on circuit board 114. Reference numerals 116a, 116b and 116c refer to the respective breakpoints of said first, second and third light barriers. Interruption transpires by way of a respective first, second and third disk provided on a first, second and third thin finger at plate-shaped region 112 of optical measuring base unit 102.

The three light barriers are respectively arranged in connecting lines corresponding to the spring elements housed in the three partially hollow lugs (indicated by dotted circles in FIG. 6), whereby the breakpoint of the associated disk lies at the respective center of said connecting lines.

This arrangement enables the determining of a tilting of the optical measuring base unit 102 relative housing 101 in all directions and thus provides for precise monitoring to ensure the parallelism of touchdown surface and measurement surface.

It is however to be noted that, in principle, other geometric arrangements of the elastic retaining means and light barrier means are also possible; e.g., rectangular, hexagonal, etc. Likewise, one sole light barrier means may also detect a tilting in only one direction. Or two light barrier means preferably arranged essentially perpendicular to one another can determine angle deviations in two dimensions.

Instead of employing light barrier means to determine position of the optical measuring base unit 102 relative housing 101, this procedure may also ensue employing, for example, inductive, capacitive or resistive detecting means. It is thus also possible, as an example, to continually measure the movement of optical measuring base unit 102. This has the advantage that one can pre-set one or several tolerance range(s) of deviation from the parallelism between touchdown surface 107 and measurement surface for the triggering of a measurement (e.g., differing calibration or precision classes).

Figure 7:
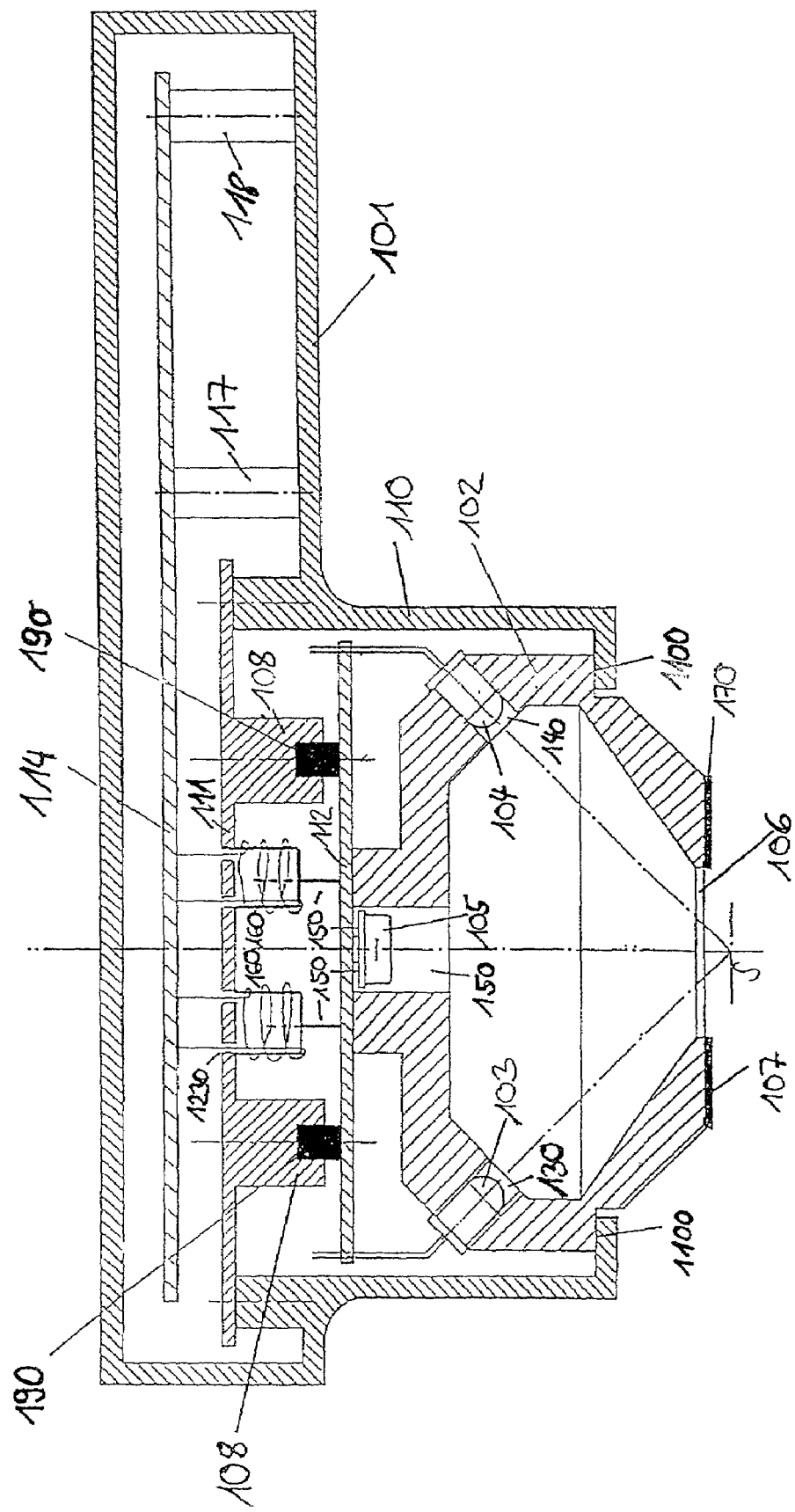
FIG. 7 a cross-sectional view of a fourth preferred embodiment of the present inventive device.

FIG. 7 shows a cross-sectional view of a fourth preferred embodiment of the device according to the present invention in which the determining of position is performed by inductive means.

The embodiment in accordance with FIG. 7 first differs from the third embodiment according to FIG. 4 in that touchdown surface 107 is provided with a Teflon coating 170 for the purpose of protecting the measurement surface. In addition, spring elements 109 in partially hollow lug 108 have been replaced by resilient hard rubber cylinders 190.

An essential difference, however, consists in that detecting of the position of the optical measuring base unit 102 is carried out by inductive detecting means 150,160.

Inductive detecting means 150, 160 consists of ferromagnetic pins 150 which are disposed at predetermined positions on the plate-shaped region 112 of the optical measuring base unit 102 and protrude upward therefrom, as well as coil detectors 160 which detect a change in inductance occurring in the downwardly open coils based on changing immersion depth of ferromagnetic pins 150. However, the respective immersion depth just reflects the position of optical measuring base unit 102 relative housing 101, by means of which the correct measurement position can then be established.

The measurement signals of coil detectors 160 are conducted through openings 1230 in carrier means 111 to circuit board 114, where processing of same ensues.

The further details of the second embodiment are the same as that of the previous embodiment.

Figure 8:
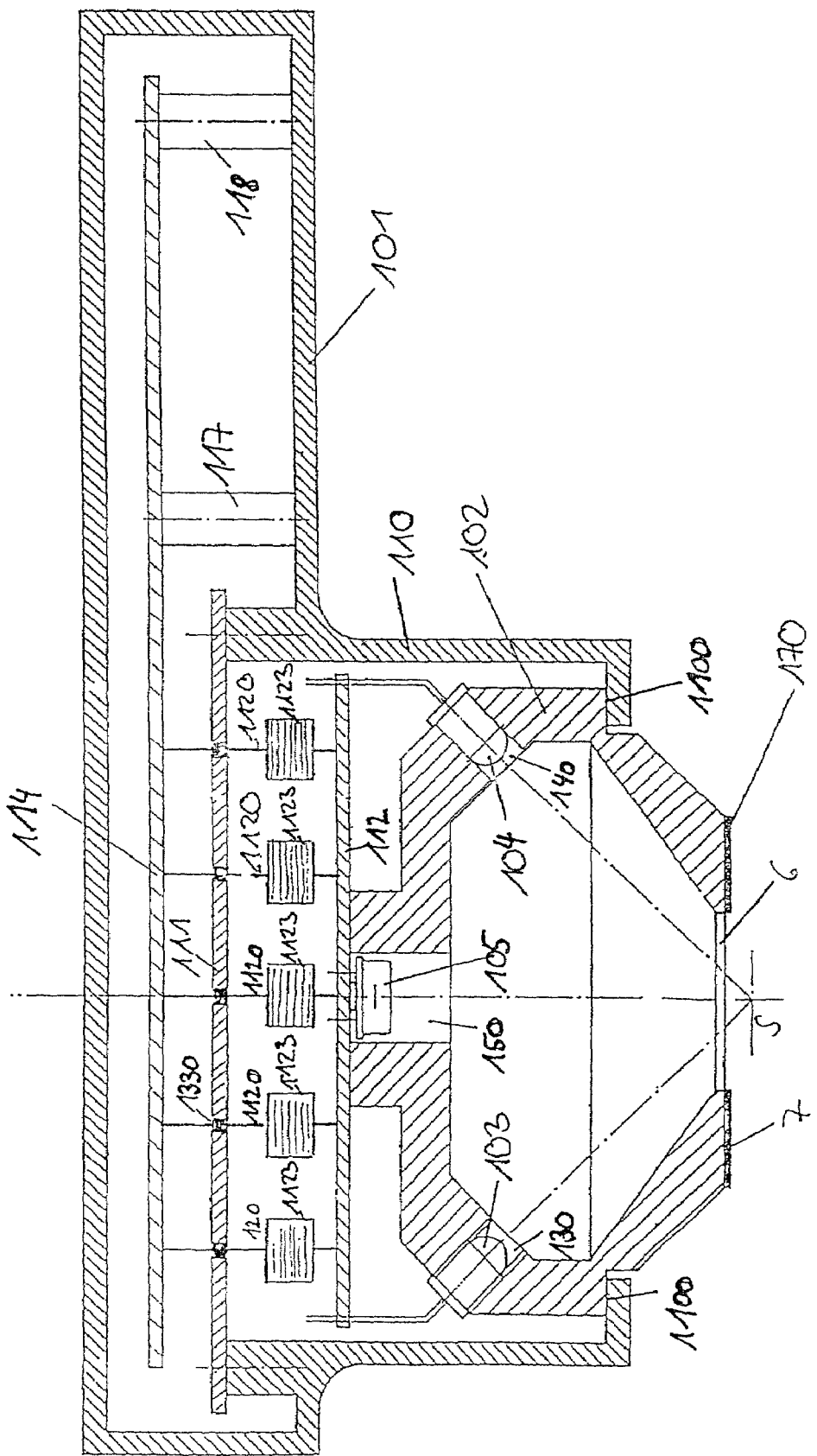
FIG. 8 a cross-sectional view of a fifth preferred embodiment of the present inventive device.

FIG. 8 shows a cross-sectional view of a fifth preferred embodiment of the device according to the present invention.

As in the fourth embodiment, the present embodiment according to FIG. 8 likewise provides for a Teflon coating 170 on touchdown surface 107.

In the third embodiment, detecting the position of optical measuring base unit 102 transpires by means of a capacitive detecting means 1120, 1123.

Capacitive detecting means 1120, 1123 consists of a capacitor means solidly anchored between the plate-shaped region 112 of optical measuring base unit 102 and carrier means 111. Said capacitor means in turn encompasses a number of single capacitors 1120 with an elastic dielectric medium 1123 situated between their capacitor plates. The output signals of said capacitors 1120 are fed to circuit board 114 through bushing 1330 for further processing.

When the device is now set upon the measurement surface for operation, elastic medium 1123 between the capacitor plates undergoes deformation and the capacitance of the individual capacitors 1120 change. It is thus possible to determine position changes of the optical measuring base unit 102 relative the housing 101.

The combination of the elastic retaining means in the form of an elastic medium 1123 between the capacitor plates of capacitors 1120 and the detecting means is of particular preference with this embodiment.

The further details of the present embodiment are the same as those from previously described embodiments.

Determining the correct measurement position is not only possible from determining a position change of the optical measuring base unit 102 relative housing 101, but can also be carried out by determining of a corresponding change in pressure.

Figure 9:
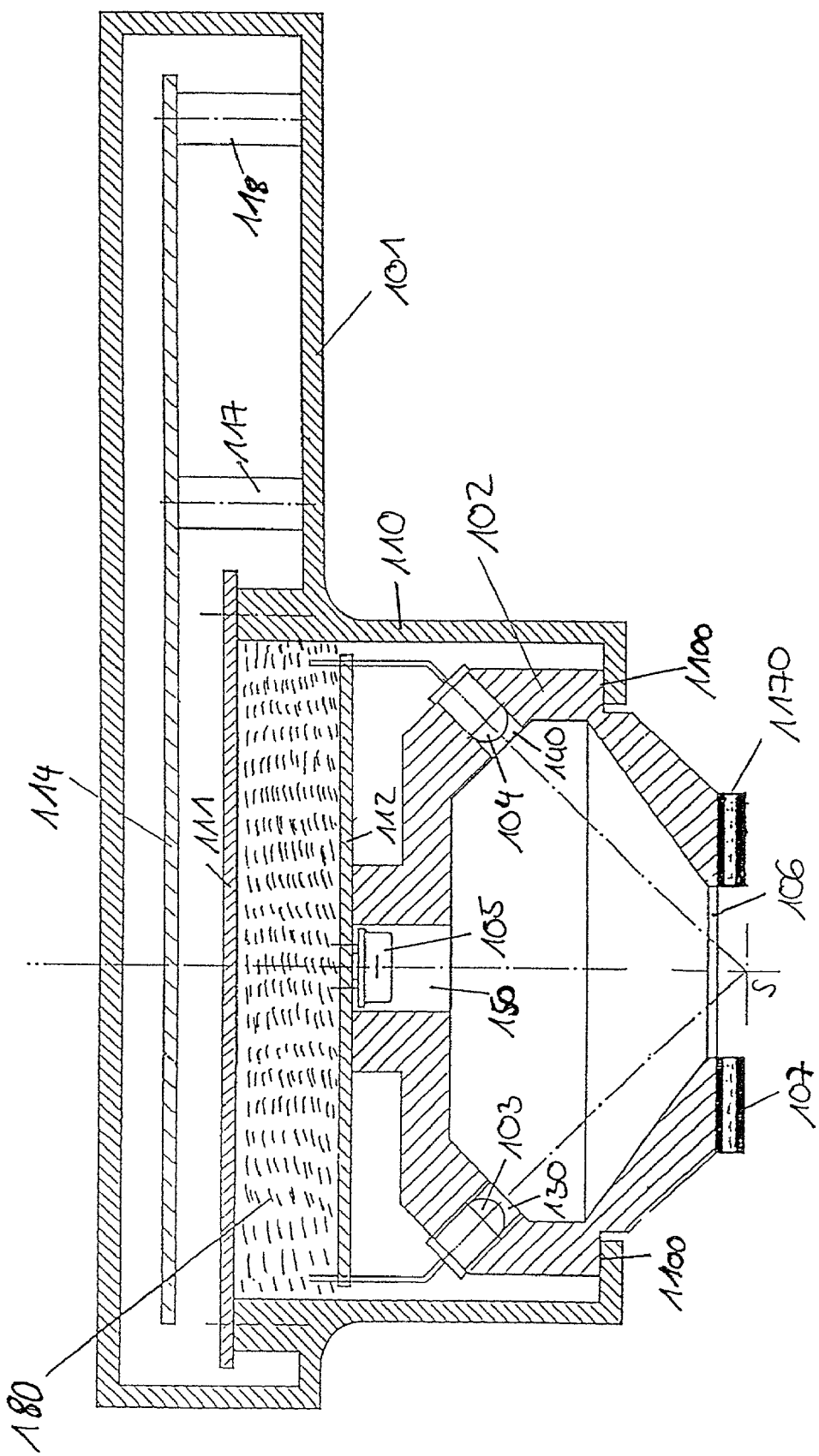
FIG. 9 a cross-sectional view of a sixth preferred embodiment of the present inventive device.

FIG. 9 shows a cross-sectional view of a further preferred embodiment of the device according to the present invention in which such a change in pressure is detected.

In the embodiment according to FIG. 9, an elastic retaining means configured as a layer of elastic medium 180 is disposed between the plate-shaped region 112 of optical measuring base unit 102 and carrier means 111. This layer may consist of, for example, a resilient durofoam material.

In contrast to the other embodiments, rather than detecting a change in position of the optical measuring base unit 102 relative housing 101 within said housing 101, a change in pressure is detected by means of a touchdown pressure detector 1170, which is disposed external said housing 101 on the touchdown surface 107 of said optical measuring base unit 102.

The output signals of said touchdown pressure detector 1170 which, for example, may function as a capacitive means, are fed over (not shown) connections to circuit board 114 for further processing.

Particularly, said touchdown pressure detector 1170 can be of such design so as to distinguish between local touchdown differences within touchdown surface 107 itself. When one knows the elasticity of the resilient retaining means, any position change of the optical measuring base unit 102 relative housing 101 can be calculated directly from the existing touchdown pressure detected by touchdown pressure detector 1170. In this manner, one therefore also receives the desired information about the correct measurement position.

The further details of the present embodiment are the same as those in the third embodiment.

As a conceivable variation of this sixth embodiment, the touchdown pressure detector may also be housed in the elastic retaining means.

It should be noted that the detecting of a position change according to the third through fifth embodiment may of course be combined with the detecting of a change in pressure according to the sixth embodiment for the purpose of even further increasing monitoring precision.

It is ultimately possible to operate the inventive device using robotic means instead of a human user whereby controlling of said robotic device ensues through the position and/or pressure changes as detected.

As clarified above, the present invention thereby provides a device for measuring visual properties, particularly visual properties of surfaces, as well as a method for operating said device which contributes to the visual characterizing of surfaces.

The invention claimed is:

1. Device for measuring reflection and transmission properties of objects and surfaces having:
   a housing;
   an optical measuring base unit comprising at least one measuring means for detecting reflection and transmission radiation by means of at least one sensor means; and
   at least one retaining means for the elastic retention of said optical measuring base unit within said housing;
   whereby said optical measuring base unit comprises at least one touchdown means for setting said optical measuring base unit down upon a surface to be measured; and
   whereby a base surface of said optical measuring base unit assumes a predetermined elastically adjustable position relative the housing in the unpositioned state.

2. Device according to claim 1, wherein said optical measuring base unit is provided for measuring at least one characteristic parameter of said measurement surface, whereby at least one of said at least one characteristic parameter is taken from among a group of parameters which includes gloss, haze, florescence, distinction of image (DOI), a representative measure of typical wavelengths and their amplitudes (orange peel) of the surface topology of said measurement surface at a predetermined wavelength interval, whereby an evaluation may also ensue at two or more wavelength ranges when determining said representative measure, and a color of said surface.

3. Device according to claim 2, wherein two, three or more characteristic parameters of said measurement surface are ascertainable.

4. Device according to claim 1, wherein said base surface of said optical measuring base unit encompasses at least one contact surface of said touchdown means with said surface to be measured.

5. Device according to claim 1, wherein said touchdown means encompasses at least one supporting means, whereby at least one of said at least one supporting means contacts said surface to be measured in the positioned touchdown state.

6. Device according to claim 1, wherein at least one supporting means comprises at least one length control means which enables an elastic length change of said supporting means.

7. Device according to claim 1, wherein at least one retaining means comprises a guiding means so that said optical measuring base unit is arranged displaceable in at least one direction in said guiding means.

8. Device according to claim 7, wherein at least one of said at least one guiding means comprises a reset means so that a resetting force is introducible to said optical measuring base unit at least in the positioned touchdown state.

9. Device according to claim 1, wherein a means is provided for determining of alignment of the base surface to the measurement surface.

10. Device according to claim 1, wherein a detecting means is provided for the detecting of at least one change in condition of the optical measuring base unit induced by touchdown on the measurement surface, whereby said change in condition is taken from among a group comprising changes in condition which encompass a change in position of said optical measuring base unit relative said housing and a change in pressure on said touchdown means.

11. Device according to claim 10, wherein said detecting means detects changes in position from at least one displacement of said optical measuring base unit at at least one point essentially perpendicular to said measurement surface.

12. Device according to claim 1, wherein an activating means is provided to activate the measuring means upon attaining a suitable alignment of said base surface and measurement surface.

13. Device according to claim 1, wherein at least one detecting means, which detects at least one change in position of said optical measuring base unit relative said housing, comprises a means for determining contingencies taken from among a group of means configured for such determinations such as capacitive measuring means for deriving changes in the capacitance of a capacitor means, inductive measuring means for deriving changes in inductance, resistive measuring means for deriving changes in resistance and force measuring means for deriving changes in the force exerted on said retaining means.

14. Device according to claim 13, wherein said detecting means detects changes in pressure occurring at the contact surface, whereby at least one detecting means is disposed as a capacitive as a local resolution detecting means.

15. Device according to claim 13, wherein said detecting means comprises at least one light barrier means, whereby at least one light barrier means emits a signal when at least a part of said optical measuring base unit undergoes a predetermined change in position.

16. Device according to claim 1, wherein at least one retaining means of said optical measuring base unit is urged by at least one compressing means toward an interior surface of said housing, whereby said compressing means is taken from among a group comprising spring means, foam and durofoam means, rubber means and helical spring means.

17. Device according to claim 1, wherein said housing has an interior transverse carrier means which at least comprises one partially hollow lug with a spring element supported therein, whereby at least one spring element presses against a part of said optical measuring base unit.

18. Device according to claim 17, wherein said transverse carrier means is disposed with an opening through which the lugs provided on the optical measuring base unit extend into the interior of the housing, and at least one of said one least light barrier means is activated by a disk means affixed to an end of said lug.

19. Device according to claim 1, wherein wheels are disposed on said housing or said optical measuring base unit.

20. Device according to claim 1, wherein said measuring base unit furthermore comprises at least one source of radiation, the radiation emitted therefrom being directed at least partially at a predetermined angle to the surface to be measured.

21. Device according to claim 1, wherein said housing can be set down upon the surface to be measured for taking a measurement such that at least one part of said housing comes into direct contact with said surface to be measured.

22. Device according to claim 1, wherein at least one part of said optical measuring base unit protrudes from said housing in unpositioned state.

23. Device according to claim 1, wherein touching said housing down upon the surface to be measured induces a displacement of said optical measuring base unit within said housing.

24. Device according to claim 1, wherein said housing encompasses at least one housing supporting means whereby said housing supporting means is in direct contact with the surface to be measured in positioned touchdown state.

25. Device according to claim 1, wherein said optical measuring base unit is pivotally arranged within said housing relative at least one pivotal axis.

26. Device according to claim 25, wherein at least one of said at least one pivotal axis is aligned essentially parallel to the surface to be measured.

27. Device according to claim 25, wherein said pivotal axis is aligned essentially perpendicular to a connecting segment between two supporting means of said optical measuring base unit, whereby said pivotal axis is preferably arranged essentially centrally between said two supporting means.

28. Device according to claim 25, wherein a clearance distance of said pivotal axis to the surface to be measured is smaller than a length of said connecting segment.

29. Device according to claim 25, wherein said pivotal axis is retained displaceably on said guiding means.

30. Device according to claim 1, wherein a length control means is provided in at least one supporting means so that the longitudinal extension of the at least one supporting means may be adjusted.

31. Device according to claim 1, wherein at least one clearance distance to the surface to be measured is determinable at at least two points of said housing or optical measuring base unit, whereby said clearances are determined through the evaluation of the signals emitted by at least one transmitting means and received by at least one receiving means, whereby at least one of said transmitting means emits signals which are taken from among a group which encompasses electromagnetic or sound waves, and whereby said evaluation ensues by utilizing a method encompassing methods of running time measurement, triangulation, or interference evaluation, whereby a representative measure of curvature for the surface is derived from said clearance.

32. Device according to claim 1, wherein a pattern projection means is provided for projecting a light pattern onto the surface to be measured in which a sensor means receives the light reflected from the measurement surface and a representative measure of curvature for the measurement surface is derived in at least one direction from evaluating the light intensity profile.

33. Device according to claim 1, wherein a tilting of said optical measuring base unit relative the surface to be measured can be determined so that measurement values can be corrected thereto.

34. Device according to claim 1, wherein at least four clearance sensors are arranged in such a manner that at least one tilting of said optical measuring base unit relative the surface to be measured can be determined and that a Wheatstone bridging circuit means is provided, the signal of which can be used to control the length control means of the supporting means so as to attain an alignment of the base surface to the surface to be measured which is within a permissible range.

35. A method for operating a device for measuring reflection and transmission properties of objects and surfaces having a housing, an optical measuring base unit comprising at least one measuring means for detection reflection and transmission radiation, by means of at least one sensor means, and at least one retaining means for the elastic retention of said optical measuring base unit within said housing, whereby said optical measuring base unit comprises at least one touch-down means for setting said optical measuring base unit down upon a surface to be measured, and whereby a base surface of said optical measuring base unit assumes a predetermined elastically adjustable position relative in the housing in the unpositioned state, comprising the steps:
   i) setting of the device down on the measurement surface;
   ii) detecting a change in condition of said optical measuring base unit relative to the housing induced by setting down of the touchdown means on the measurement surface;
   iii) determining whether said change in condition indicates a permissible alignment of said base surface and said measurement surface; and
   iv) activating of a measurement when said change in condition indicates a permissible range for the alignment of said base surface and said measurement surface.

36. Method according to claim 35, with the step:
   deactivating of a measurement when said change in condition exceeds a predefined tolerance deviation from the permissible alignment of said base surface and said measurement surface.

37. Method according to claim 35, with the step:
   emitting of a warning signal when said change in condition exceeds a predefined tolerance deviation from the permissible alignment of said base surface and said measurement surface.

* * * * *